US006852101B2

United States Patent
Damaghi et al.

(10) Patent No.: US 6,852,101 B2
(45) Date of Patent: Feb. 8, 2005

(54) LIQUID ABSORBENT PAD HAVING A SINGLE LARGE THROUGH SLIT AND ABSORBENT ARTICLE COMPRISING SAME

(75) Inventors: Babak Damaghi, Kings Point, NY (US); Hamzeh Karami, Lockhaven, PA (US)

(73) Assignee: First Quality Products, Inc., State College, PA (US)

( * ) Notice: Subject to any disclaimer, the term of this patent is extended or adjusted under 35 U.S.C. 154(b) by 360 days.

(21) Appl. No.: 10/066,721

(22) Filed: Feb. 4, 2002

(65) Prior Publication Data

US 2003/0149412 A1 Aug. 7, 2003

(51) Int. Cl.[7] .............................................. A61F 13/15
(52) U.S. Cl. .............................. 604/385.101; 604/378; 604/383; 604/385.01
(58) Field of Search ................................ 604/378–380, 604/385.01, 385.101, 385.28, 385.29, 383

(56) References Cited

U.S. PATENT DOCUMENTS

| 3,889,679 | A | | 6/1975 | Taylor |
| 5,176,672 | A | * | 1/1993 | Bruemmer et al. ..... 604/385.19 |
| 5,300,053 | A | | 4/1994 | Genaro |
| 5,562,650 | A | * | 10/1996 | Everett et al. ............... 604/378 |
| 5,716,351 | A | * | 2/1998 | Roe et al. .............. 604/385.21 |

FOREIGN PATENT DOCUMENTS

WO    WO 91/09582    *  7/1991    ........... A61F/13/16

* cited by examiner

*Primary Examiner*—Jacqueline Stephens
(74) *Attorney, Agent, or Firm*—Amster Rothstein & Ebenstein LLP (57) ABSTRACT

A disposable absorbent article is provided comprising a liquid absorbent pad having a large single through slit designed to control fluid surge and minimize fluid leakage when fluid is discharged suddenly during the use of the article.

17 Claims, 8 Drawing Sheets

LIQUID ABSORBENT PAD HAVING A SINGLE LARGE THROUGH SLIT AND ABSORBENT ARTICLE COMPRISING SAME

FIELD OF THE INVENTION

The present invention relates to a liquid absorbent pad having a single large through slit for use in absorbent articles such as diapers, briefs, incontinence garments, sanitary napkins, and the like articles. The invention also relates to absorbent articles comprising a liquid absorbent pad or layer having a single through slit designed to control the fluid surge in order to prevent or minimize fluid leak when fluid is discharged suddenly during the use of the absorbent article.

BACKGROUND OF THE INVENTION

It is common knowledge that incontinent persons, many elderly and infants have difficulty controlling urination and often discharge or excrete large amount of urine suddenly, thus causing a fluid surge in the crotch area. Uncontrolled fluid surge results in leakage of fluid unless the absorbent article is especially constructed to contain the fluid surge in order to prevent or minimize fluid leakage.

Several different structures have been disclosed for absorbent articles in an effort to control or ameliorate the adverse effects of fluid surge in absorbent articles used by incontinent persons, the elderly and infants. One early patent, i.e., U.S. Pat. No. 3,889,679 issued Jun. 17, 1975 to Glenn N. Taylor, III, describes a disposable diaper which comprises a liquid impervious backing sheet and an absorbent body having a multiplicity of openings therein which extend through said absorbent body thus defining a corresponding multiplicity of fluid passages. The surging fluid flows directly through the absorbent body toward the liquid impervious backing sheet remote from the absorbent body. The passages are cylindrical, have a diameter of from about ¼ to about 1-inch and are provided through the full extent of the absorbent body.

In a more recent patent, i.e., U.S. Pat. No. 5,300,053 issued Apr. 5, 1994 to Donald M. Genaro, an absorbent brief is described which comprises a liquid-permeable top layer, a liquid-impervious backing layer and absorbent layer sandwiched between said two layers. The absorbent layer has a dispersion channel which extends through the absorbent layer to the liquid-impervious layer for providing unobstructed liquid flow. As shown in FIG. 1 of the Genaro patent, liquid flowing through the distribution channel 18 can be channeled to secondary channels 18', 18" which, together with distribution channel 18, form a generally Y-shaped channel.

Others have proposed structures for absorbent articles which rely on increased volume of the absorbent pad to absorb the surging fluid and minimize or prevent fluid leak. However, increased volume of absorbent pad contributes to bulkiness of the article which results in inferior fit around the body of the wearer.

It has also been suggested to use an absorbent pad made of a high absorbency material, or use superabsorbent polymers (SAP) in the absorbent pad but these alternatives are costly even if the bulkiness of the article is not increased. Others have incorporated an acquisition layer having a basis weight of 50–100 grams per square meter (GSM) in the structure of the absorbent article in order to reduce the "insult time" but this results in increased cost of the article.

There is thus a dire need for an absorbent pad for use in diapers, incontinent briefs and the like articles, which is effective for minimizing or preventing fluid leakage caused by sudden fluid surge in and around the crotch area.

It is therefore an object of the present invention to provide a liquid absorbent pad for use in absorbent articles, wherein the absorbent pad has a unique construction designed to accommodate and contain fluid surge caused by sudden urination.

It is, another object of this invention to provide a liquid absorbent pad useful in absorbent articles wherein the absorbent pad has a single large through slit for accommodating fluid surge and minimizing fluid leaks from the crotch area of the absorbent article.

It is also an object of this invention to provide a disposable absorbent article such as diapers, briefs, incontinence garments, sanitary napkins, and the like articles comprising such liquid absorbent pads.

It is a further object of this invention to provide a disposable absorbent article which, due to its unique structure of the absorbent pad, helps maintains the top surface of the article dry after a surge of fluid such as by sudden urination.

The foregoing and other objects of the present invention will be more fully comprehended from the following detailed description of the invention with reference to the accompanying drawings.

SUMMARY OF THE INVENTION

In accordance with this invention, a disposable absorbent article is provided which comprises a liquid absorbent pad (core or layer) which has a large elongated through slit designed to prevent leakage of fluid, usually urine, caused by sudden discharge of copious amount of urine by incontinent persons, the elderly, or by infants when using the article. The disposable absorbent article, e.g., a diaper, comprises a liquid pervious topsheet, a liquid-impervious backsheet which, when breathability is required is vapor pervious, a crotch region and a liquid absorbent pad made of a material comprising fluff and super-absorbent polymer (SAP), disposed between the topsheet and the backsheet. The liquid absorbent layer also comprises a crotch region (pad crotch area) and has a top surface and a bottom surface, and a single large through elongated slit which extends from the top surface to the bottom surface of the absorbent pad. The slit dimensions is preferably from about 0.5 inch to about 1.5 inches wide, and from about 2 to about 10 inches long depending on the size of the diaper, and is located within the pad's crotch region.

The liquid absorbent pad is defined by a pair of opposed longitudinal sides and a pair of opposed lateral sides and the slit is also defined by a pair of opposed longitudinal sides and a pair of opposed lateral sides. The region between the sides of the slit and the sides of the pad define a zone enriched with fluff-SAP mixture such that this region contains more fluff-SAP mixture than the remaining portion of the pad, i.e., the non-enriched zone. This fluff-SAP mixture concentration in the vicinity of, or adjacent the sides of the slit insures more effective liquid absorption.

BRIEF DESCRIPTION OF THE DRAWINGS

In the drawings, wherein like reference numerals are employed to designate like parts wherever possible.

DETAILED DESCRIPTION OF THE INVENTION

Figure 1:
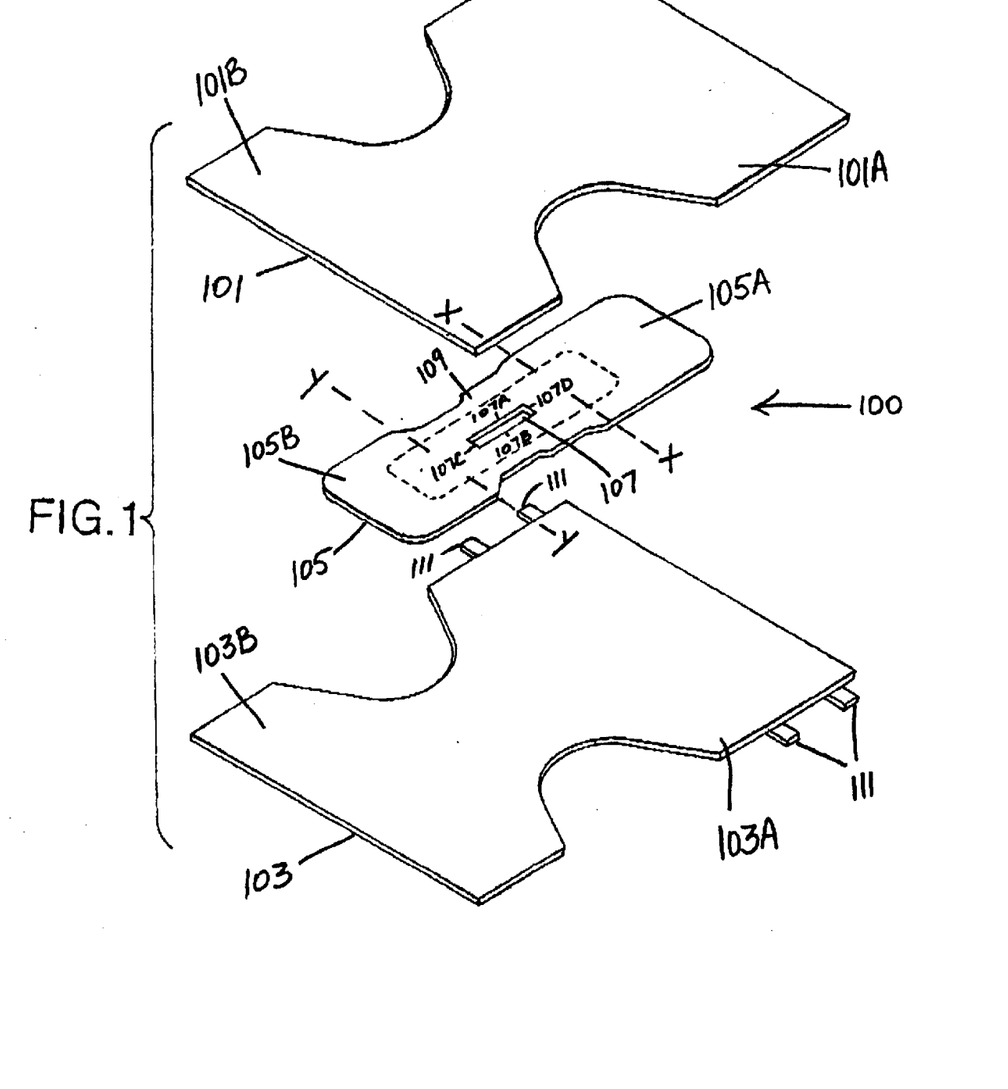
FIG. 1 is an exploded view of an absorbent brief including an absorbent layer having a single large through slit formed therein in accordance with one embodiment of the present invention.

Referring first to FIG. 1 of the drawings, there is shown an absorbent article such as a diaper 100 having a liquid permeable topsheet or layer 101, a liquid impervious backsheet or layer 103 and an absorbent layer 105 sandwiched between the topsheet 101 and the backsheet 103. The diaper shown in FIG. 1 is in an hour-glass shape, though it can be formed in butterfly shape or in other configurations. The topsheet 101 includes a back waist section or panel 101A and a front waist section or panel 101B, and the backsheet 103 includes a rear waist section or panel 103A and a front waist section or panel 103B. The absorbent layer 105 comprises a single through elongated slit 107 formed therein and extending from the top surface through the bottom surface of said layer. The absorbent layer comprises a back panel 105A and a front panel 105B, and may be in a generally rectangular configuration, or it may be T-shaped or in hour-glass shape as the brief itself. Regardless of the shape of the absorbent layer, as will hereinafter be described the size and location of the single through aperture 107 are critical in controlling the fluid surge resulting from sudden discharge of copious amounts of urine which is often experienced by incontinent persons, the elderly and the infants. For maximum fluid surge control and leak prevention, the slit 107 is from about 2 to about 10 inches long and is from about 0.5 to about 1.5 inches wide, and is located entirely within the crotch region 109 which region is between the broken lines x—x and y—y in FIG. 1. Referring back to FIG. 1, the backsheet is provided with tabs 111 for securing the rear and front panels together when folded to form the diaper. Tabs 111 may be adhesive tabs, Velcro®, fasteners or other conventional engagement means.

The absorbent layer 105 is made of conventional absorbent material known to those skilled in the art such as wood pulp fiber and various types of wettable hydrophilic and cellulosic fibers, all of which are used in the form of "fluff". Examples of suitable fibrous materials forming the fluff are described in the aforementioned Taylor patent and in U.S. Pat. No. 5,429,629 issued Jul. 14, 1995 to Margaret G. Latimer et al., the disclosures of which are incorporated herein by reference. It is to be understood that the term "fluff" refers to all those fibrous materials disclosed in said patents. While absorbent pads made of fluff exhibit adequate fluid absorption capacity, improvement in fluid absorption is realized by mixing the fluff with Super Absorbent Polymers (SAP) in which the SAP constitutes from about 3 to about 80 weight percent of the fluff-SAP mixture. It has been found that a more effective fluid surge control may be realized when the fluff-SAP mixture is more concentrated in a fluid surge management zone (Z) which is defined by the broken lines around the absorbent layer 105 as shown in FIG. 1. By increasing the amount of the fluff-SAP mixture in this zone, greater efficiency is realized in containing the sudden surge of fluid which results from uncontrolled urination by incontinent persons, the elderly or by infants. In a typical institutional or household diaper used by adult incontinent persons, the diaper is usually from about 24 to about 40 inches long and from about 17 to about 35 inches wide, and the absorbent layer is from about 19 to about 35 inches long, from about 14 to about 20 inches wide and is from about 100 to about 400 mils thick. The slit 107 must be located within the crotch region, preferably centrally and is defined by the longitudinal sides 107A, 107B and the lateral sides 107C, 107D which are generally parallel to the respective longitudinal and lateral sides of the zone Z. It has been found that maximum fluid surge control can be realized when the longitudinal sides of zone Z are spaced from about 1 to about 10 inches relative to the respective longitudinal sides 107A, 107B of the slit 107, and the lateral sides of zone Z are spaced from about 6 to about 30 inches relative to the lateral sides 107C, 107D of the slit 107. It is this zone Z that must be enriched in fluff-SAP content relative to the remaining portion of the absorbent layer. In order to realize the advantages of the present invention, the amount of fluff-SAP mixture enriched zone is from about 1.5 to about 5.0 preferably from about 2.0 to about 3.0 times the amount of the fluff-SAP mixture in the non-enriched zone. Thus, the amount of fluff-SAP mixture in the enriched zone can vary from about 400 to about 1000 gsm, preferably from about 600 to about 800 gsm and the amount of fluff-SAP mixture in the non-enriched zone is from about 100 to about 300 gsm.

The Super Absorbent Polymers which are suitable for the purpose of this invention are generally well known in the art and are described in the aforementioned Latimer et al. patent. These include polyacrylamide, polyvinyl alcohol, polyvinyl ether, ethylene, maleic anhydride copolymers, polyacrylates, polyacrylamides, polyvinylpyrrolidone, polyacrylates, isobutylene maleic anhydride copolymers, or mixtures of said polymers and copolymers. Crosslinked polyacrylic acid has been found to be particularly effective absorbent when mixed with fiberized wood (fluff) in an amount between about 3 to about 80 weight percent based on the weight of fluff-SAP mixture.

Figure 4:
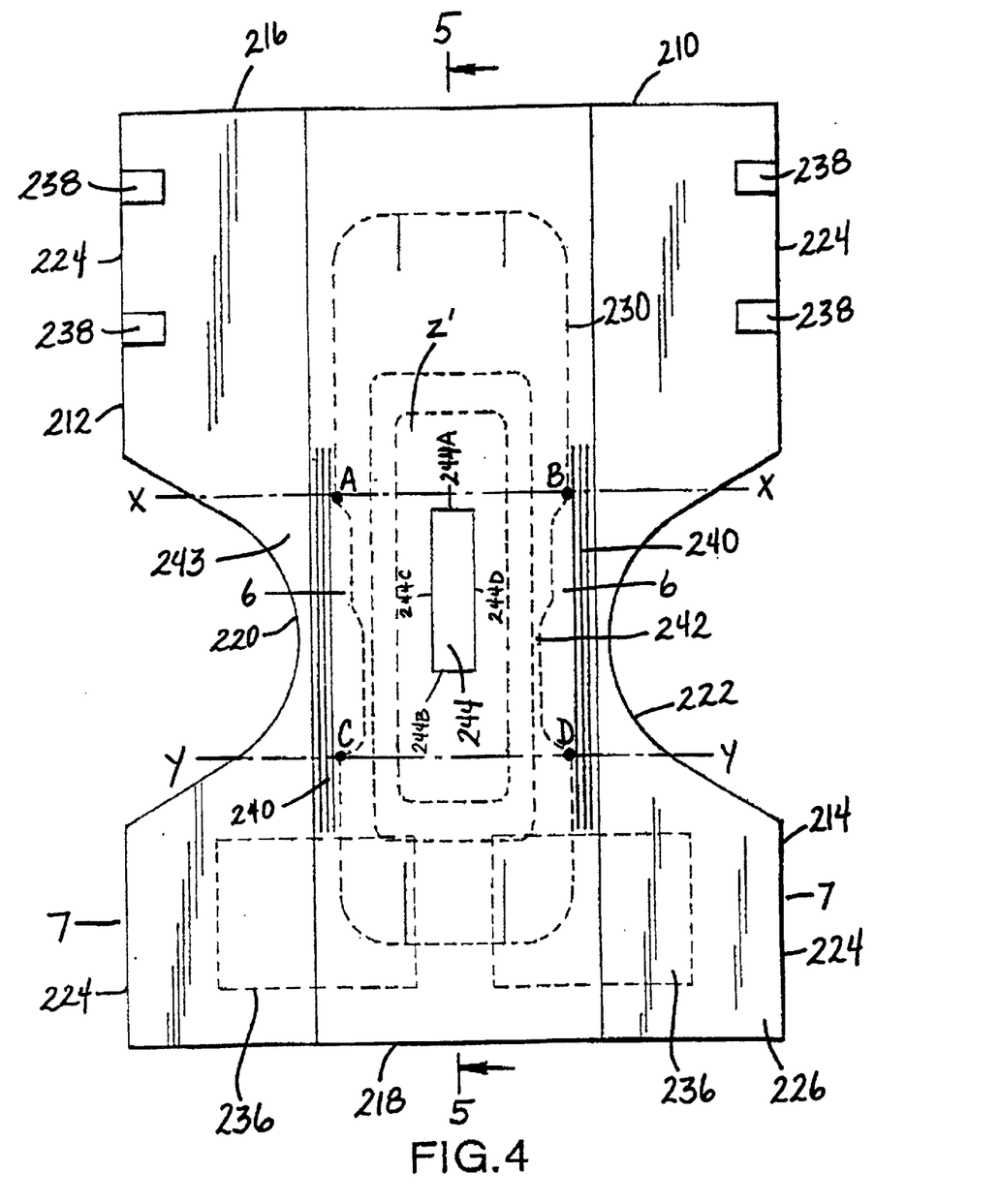
FIG. 4 is a stretched plan view of a breathable absorbent brief (diaper) incorporating an absorbent layer having a single large through slit formed therein in accordance with the embodiment shown in FIG. 1, wherein both the diaper and the absorbent pad are defined by contoured sides.
Figure 5:
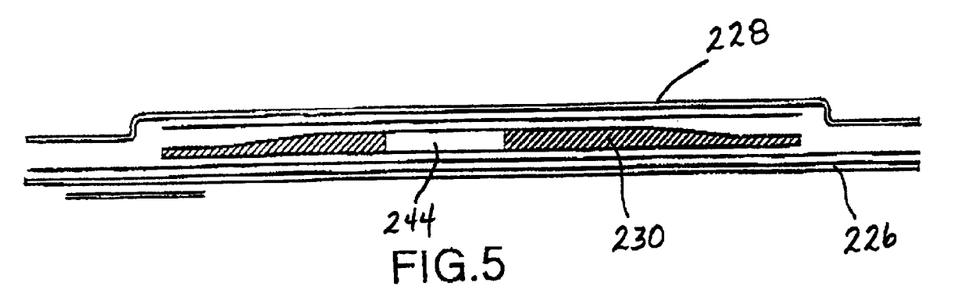
FIG. 5 is a sectional view taken along the line 5—5 in FIG. 4.
Figure 6:
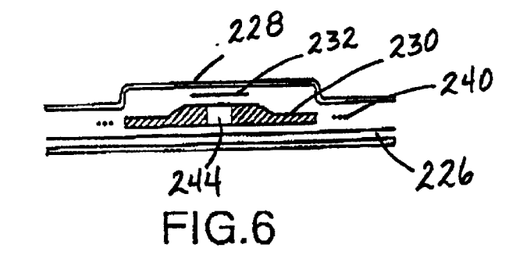
FIG. 6 is a sectional view taken along the line 6—6 in FIG. 4.
Figure 7:
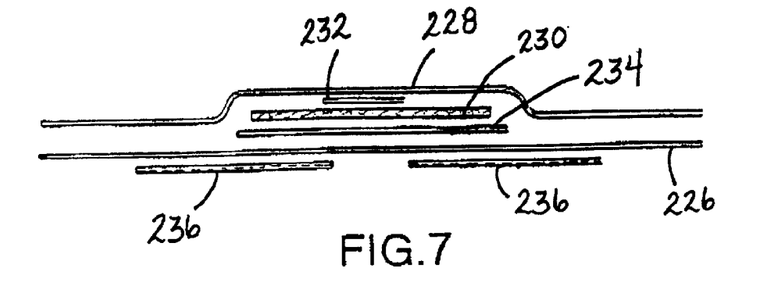
FIG. 7 is a sectional view taken along the line 7—7 in FIG. 4.

FIG. 4 illustrates a diaper in flat-out (stretched) position such as the diaper shown and described in copending application Ser. No. 09/302,385 filed Apr. 30, 1999 which is assigned to the assignee of the present application, except that the diaper in FIG. 4 herein includes an absorbent layer or pad having a single through slit in accordance with the present invention. The diaper shown in FIG. 4 is generally designated as 210 which is defined by the opposed side edges 212 and 214, the back end edge 216 and front end edge 218 which connect the side edges. Each of the side edges 212 and 214 has a medial cutout portion which defines the leg openings 220 and 222 for insertion of the legs of the wearer therethrough when the back end edge 216 is folded onto the front end edge 218 to form the diaper structure as it is worn by the user. As is further shown in FIG. 4, each of the side edges 212 and 214 has laterally extending side ears or panels 224. The diaper 210 also comprises a breathable backsheet 226, a fluid pervious front or top sheet 228 facing the body of the wearer and an absorbent pad or layer 230 disposed between the top sheet and the back sheet as shown in FIGS. 5–7. The top sheet is generally coextensive with the backsheet although this is not strictly necessary. Also shown in FIGS. 5, 6 and 7, is an acquisition layer 232 interposed between the top sheet 228 and the absorbent pad 230. The acquisition layer serves to temporarily retain the body exudates and slowly distribute them through the absorbent pad 330 in order to keep the skin dry and reduce diaper leakage. Referring again to FIGS. 5–7, the composite layers also include the layer 234, generally made of liquid and vapor impermeable polyethylene, which preferably spans the length of the absorbent article and extend laterally toward the sides of the diaper, ending at the cutout portions (leg holes) 220,222. The polyethylene film 234 may be laminated to the backsheet 226 as seen from FIGS. 5–7 and thus provides an area which is liquid and vapor impervious. As a process aid, a tissue layer may be interposed between the absorbent layer 230 and the backsheet 226.

Figure 2:
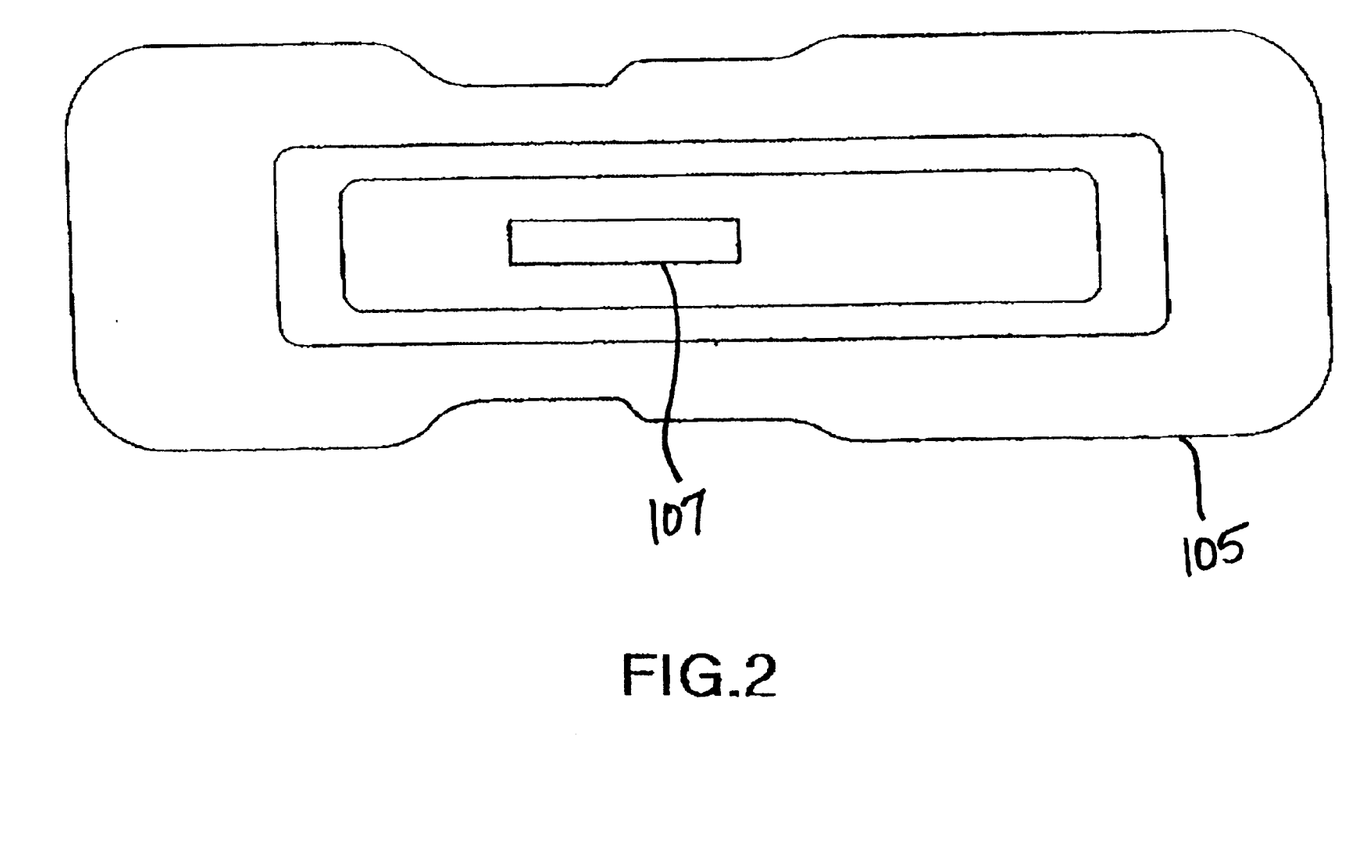
FIGS. 2 and 3 each shows a top view of an absorbent layer illustrating a different embodiment of the pad of this invention for use in an absorbent brief such as the absorbent brief shown in FIG. 1.

Referring again to FIG. 4, the backsheet 226 is provided with a pair of opposed, perforated (or non-perforated) films or landing zones 236, usually made of flexible polyolefin plastic such as polyethylene or polypropylene, a polyester, a cellulose ester or some other plastic material known in the art, but preferably it is made of polyethylene or polypropylene. A pair of releasable tabs, e.g., adhesive tabs 238 are provided at the rear side panels or ears 224 such that when the back waist end 216 is folded onto the front waist edge 218 of the diaper, the tabs 238 are securely adhered onto the corresponding surfaces of the landing zones 236. Thus, each landing zone 236 has an inside surface which is adherent to the backsheet 226, and an exterior surface which is adapted to be releasably fastened to the tabs 238. To this end, the exterior surface of each landing zone 236 may be treated with silicone or other suitable material so as to render its surface releasably adherent to the tabs 238. Instead of using a release agent or in combination therewith, the exterior surfaces of the landing zones may be embossed in order to reduce the adhesion forces between the fastening tabs and the exterior surfaces of these zones. It can be seen therefore that in use, when the back waist panel 216 is folded onto the front waist 218 the releasable tabs 238 can be fastened at any point on the surfaces of the landing zones 236 thus affording adjustment and improved fit of the diaper around the waist of the wearer. Although two perforated landing zones are shown in FIG. 2, one or more such zones may be provided which may or may not be perforated, as desired. However, perforated landing zones impart breathability to the diaper.

The diaper 210 also comprises at least one or more elastic members or bands 240 disposed near the opposite sides 212 and 214. Preferably 2 to 4 such elastic bands are used and act as "gatherers" in the crotch region 242. These elastic members are sometimes referred to in the art as crotch elastics and serve to prevent fluid leakage from the crotch area through the leg openings of the diaper. The elastic bands 240 are usually under tension and are adhesively secured at the sides of the article between the top or cover sheet 228 and the polyethylene backing film 234.

Figure 4A:
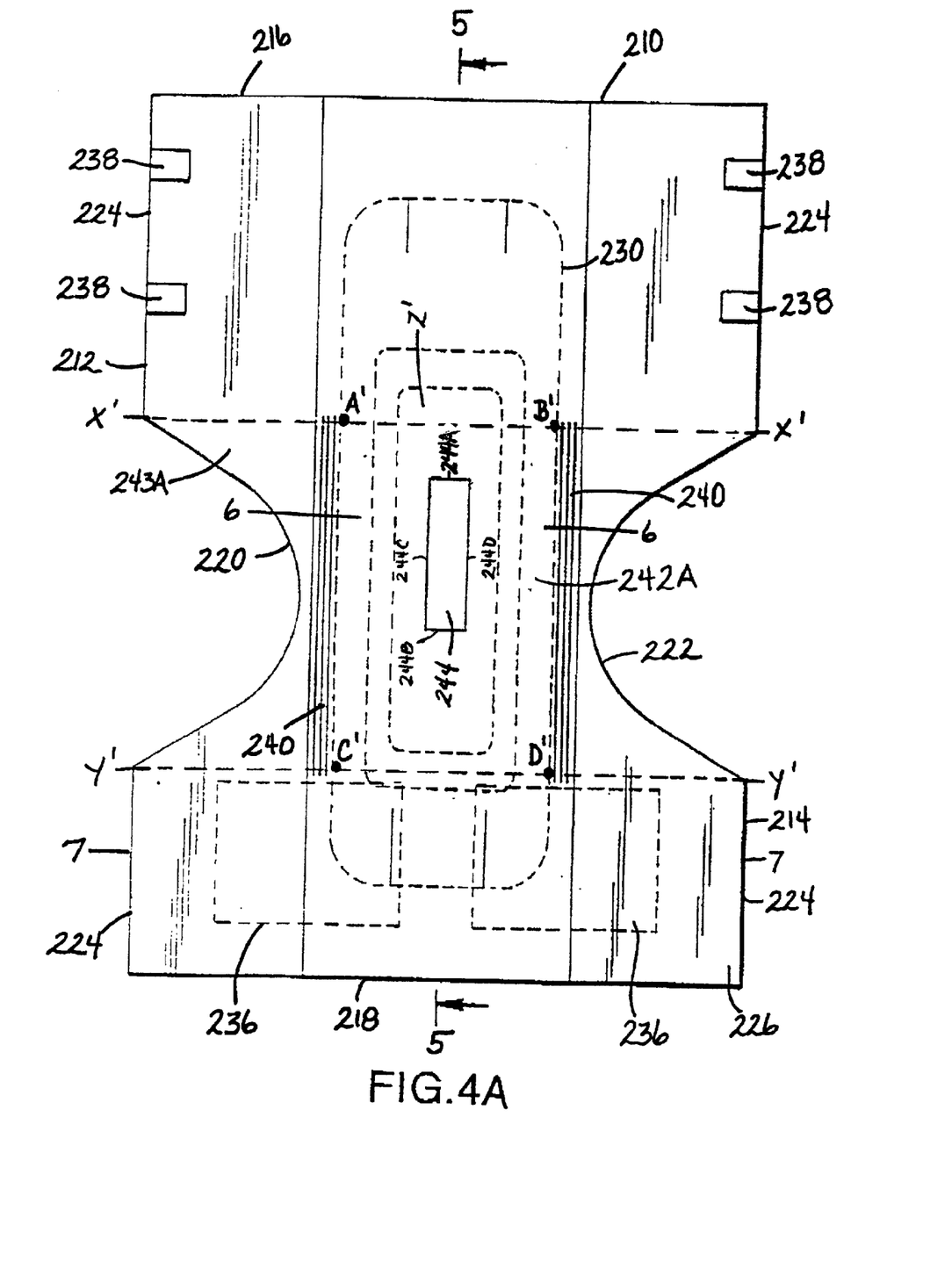
FIG. 4A is similar to FIG. 4 in all respects except that only the diaper is contoured.
Figure 4B:
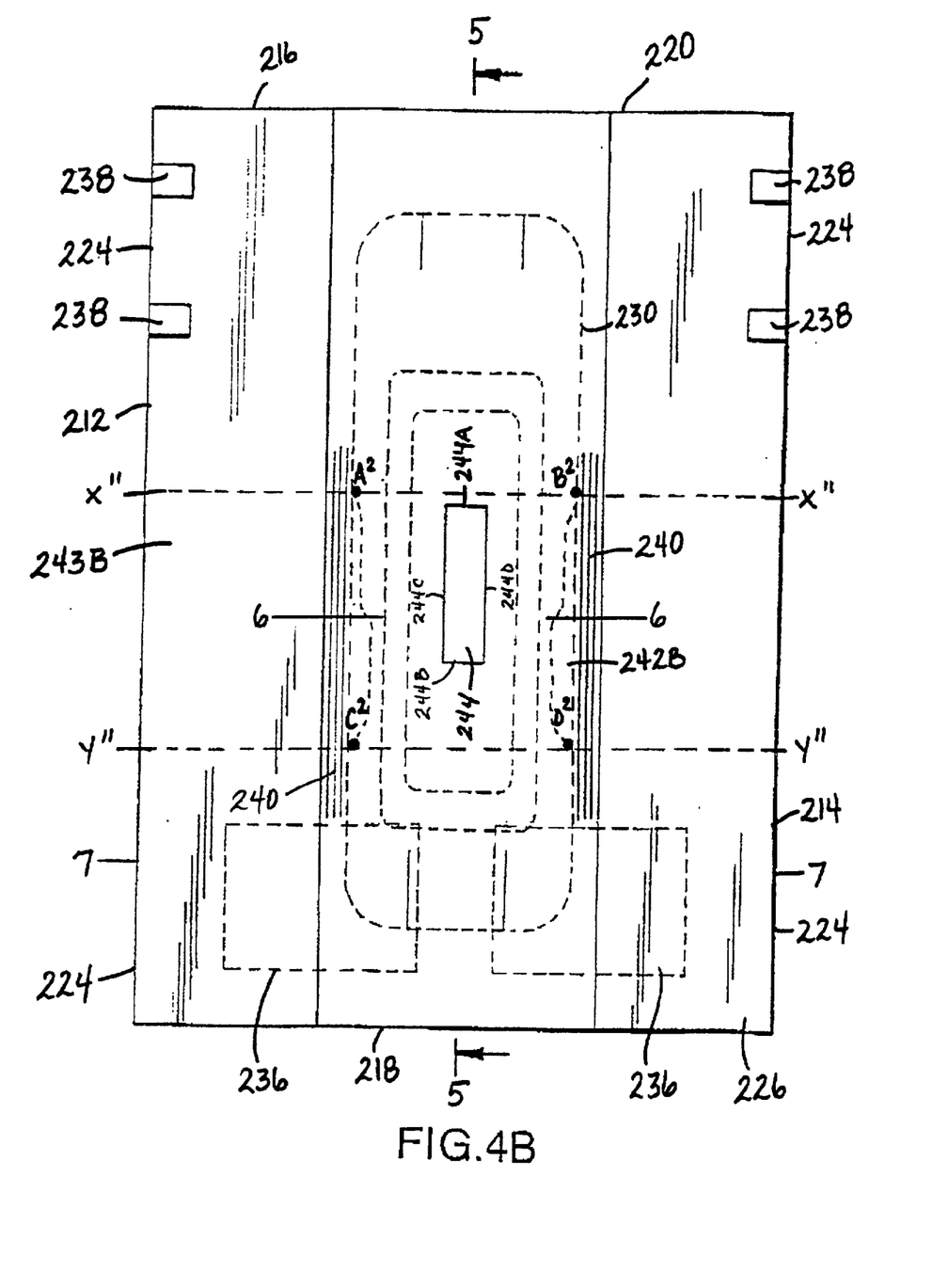
FIG. 4B is similar to FIGS. 4 and 4A in all respects except that only the absorbent layer is contoured.
Figure 4C:
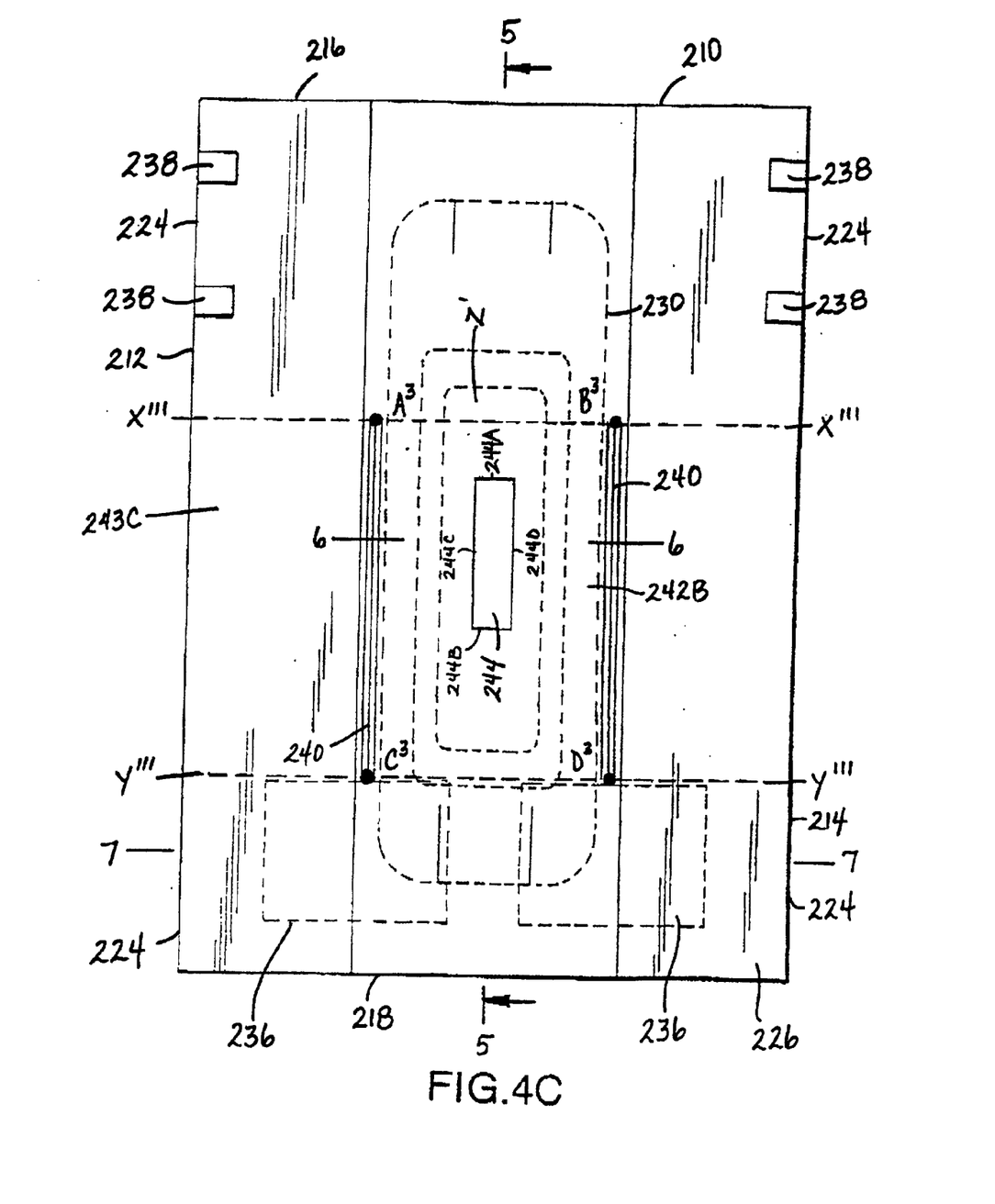
FIG. 4C is similar to FIGS. 4, 4A and 4B in all respects except that neither the diaper nor the absorbent layer is contoured.

In accordance with this invention, the absorbent pad 230 has a single through elongated slit 244 formed therein which is generally rectangular shaped although it may have some other geometrical shape such as, e.g., oval. In order to realize the advantages of the present invention the slit 244 is disposed within the crotch region 242 of the absorbent pad when the diaper and the absorbent pad have the configurations shown in FIG. 4. This region is the area defined by the points A, B, C and D which are formed by intersection of the line x—x and y—y and the longitudinal sides of the absorbent pad 230. Thus, the crotch region of the absorbent pad 230 must be distinguished from the crotch region 243 of the diaper shown in FIG. 4. It can be appreciated therefore that the crotch region 242A in FIG. 4A is the area defined by the points A', B', C' and D' formed by intersection of the lines x'—x' and y'—y' with the longitudinal sides of the absorbent pad 230, and this crotch region is to be differentiated from the diaper crotch region 243A. In FIG. 4B, the pad crotch region 242B is the area in the pad defined by the points A', B', C' and D' formed by the intersection of the lines x"—x" and y"—y" with the longitudinal sides of the absorbent pad. Again this region is to be distinguished from the diaper crotch region 243B. Similarly in FIG. 4C, the pad crotch region 242G is the area defined by the points $A^2$, $B^2$, $C^2$ and $D^2$ formed by the intersection of the lines x"—x" and y"—y" with the longitudinal sides of the pad 230, and is to be distinguished from the diaper crotch region 243C. Finally, in FIG. 4C the pad crotch region 242C is the area in the pad defined by the points $A^3$, $B^3$, $C^3$ and $D^3$ formed by the intersection of the lines x"—" and y"—y" with the longitudinal sides of the pad 230. Once again, the pad crotch region 242C is to be distinguished from the diaper crotch region 243C.

The advantages of the present invention are best realized when the elongated slit is within the pad crotch region.

Figure 3:
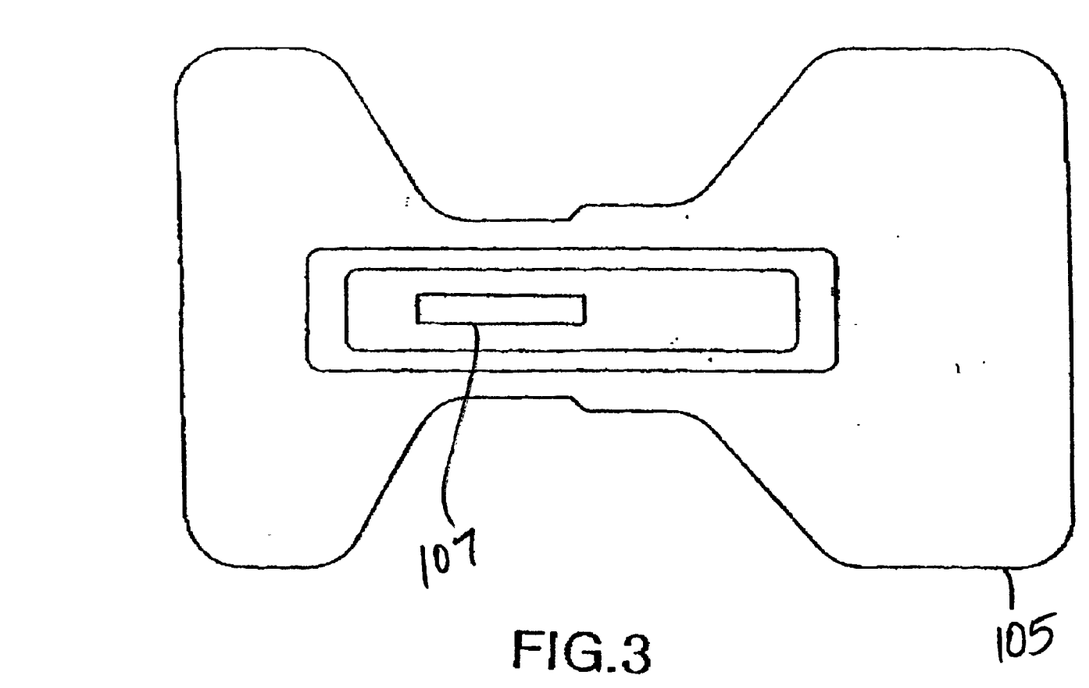

The slit 240 according to the present invention is from about 2 to about 10 inches long and from about 0.5 to about 1.5 inches wide. In FIG. 4, the slit 244 is defined by the longitudinal generally parallel sides 244A, 244B and the lateral generally parallel sides 244C, 244D, and is cut through the entire thickness of the absorbent pad which is usually about 100 to about 400 mils thick. It must be mentioned that the preferred location of the slit 244 depends on the expected wearers of the diaper. Thus, when the diaper is to be used by incontinent elderly men, or by infants, the slit is located at the middle of the pad crotch region, whereas in diapers expected to be worn by incontinent females, the slit is off the center of the pad crotch region, closer to the back edge of the absorbent pad, but still entirely within the pad crotch region. FIGS. 2 and 3 illustrate absorbent pads in which the slits are formed slightly off from the middle of the pad crotch region. In FIG. 3, the absorbent pad is shown as a butterfly shape pad. However, the shape of the pad does not reduce the efficacy of fluid surge management of the absorbent pad.

The superior surge management control efficacy of an absorbent pad having a single through slit of 5 inches long and 1 inch according to the present invention was compared to an absorbent pad without an aperture. The structure and construction of the pads were otherwise similar and each pad was incorporated in a similar size diaper. The tests were designed to determine the "insult" rate, i.e., the rate of penetration of fluid into the absorbent core. Leakage from the crotch region of the diaper is less when urine penetrates faster into the absorbent core. Thus, the shorter this time, the lower is the insult rate and the less the fluid leakage from the diaper. The test procedure and equipment used are described below.

1. Scope and Purpose:
   1.1 To measure the ability of an incontinence product to accept and retain synthetic urine under simulated in-use conditions of load and pressure.
   1.2 To calculate amount of time required for an absorbent article to absorb a fixed quantity of a test solution and to measure the dryness of the product.
2. Definitions:
   2.1 Rewet or dryness: amount of wetness returned to the surface of an incontinent product onto an absorbent filter paper.
3. Reagents:
   3.1 0.9% Sodium Chloride (NcCl) Solution
   3.2 0.01% Fuchsin Acid (Optional)-dye used for coloring Sodium Chloride solution.
4. Equipment:
   4.1 125 ml separatory funnel, discharging 7 ml/sec
   4.2 NIST Traceable Timer
   4.3 Weights
      4.3.1 Stainless steel cylindrical weight 9.8 lbs.: 9.0 cm diameter 1.0 psi
   4.4 Dosing Rings
      4.4.1 Stainless steel ring (60 mm ID, 70 mm OD, 40 mm Height) 300
   4.5 Filter paper: AFI Grade 950, 9.0 cm diameter or equivalent filter paper
   4.6 Ringstand with Support Ring
   4.7 100 ml volume graduated cylinder
   4.8 10 ml volume graduated cylinder
   4.9 Analytical Balance able to weight to nearest 0.01 grams.
5. Procedure:
   5.1.1 Trim the leg gathers, if present, out of the product so the product may lay flat.
   5.1.2 Fold under the front and back wing flaps, leaving product target area flat and in contact with test surface area.
   5.1.3 TEST PROCEDURE:
      5.1.3.1 Measure out volume of test solution with graduated cylinder and transfer the solution to the separatory funnel. If using the ring stand make sure the funnel is secured on the stand and properly suspended from the support ring.
         5.1.3.1.1 Volume 100 ml test solution for Briefs, 2-Piece, Protective Underwear, and Belted Garments.
      5.1.3.2 Center the dosing ring over the target zone, centrally located with tip of funnel approximately 40 mm from the sample surface (same height as top of dosing ring).
         5.1.3.2.1 The target zone for briefs and 2-piece undergarments is at the center of the crotch area.
         5.1.3.2.2 The target zone for protective underwear is the center of the narrowest crotch width of the pad.
      5.1.3.3 Deliver the test solution into the ring by fully opening the stopcock on the funnel. At the same time, start the timer to record speed in seconds for the test solution to completely enter the product. Stop the timer when all solution has passed through the top sheet and record the time. This is the Acquisition Speed.
      5.1.3.4 Wait fifteen (15) minutes +/− 1 minute using timer.
      5.1.3.5 Place a stack of pre-weighed filter papers (10–15 filter papers, W1) on the center of the wetted target area.
      5.1.3.6 Place a 1.0 psi cylindrical weight (9.0 cm, 9.8 lb. Equals 1.0 psi) on the top of the dry filter paper, making sure the stack is level, not tipping to one side or the other. Start the timer.
      5.1.3.7 After one (1) minute, remove the cylindrical weight and the wetted out papers.
      5.1.3.8 Reweigh the filter paper stack (W2) and record the wet filter paper weight.
      5.1.3.9 Note: if the entire stack of filter paper is wetted, the test is invalid and must be reevaluated with a new sample of using a heavier (5.0 g additional) stack of dry filter paper.
   5.1.4 MULTIPLE DOSE REWETS
      5.1.4.1 Repeat sections 5.1.3.1 through 5.1.3.9 up to two (2) more times on the same product.
   5.4 CALCULATIONS
      5.4.1. REWET (g) = W2 (Wet filter paper weight) − W1 (Dry Filter paper weight)

The test results are shown in Table 1 below, using two similar diapers except that one was without a slit and the other with a 1.5 slit.

TABLE 1

|  | Control diaper without slit | Diaper with slit as in FIG. 3 |
| --- | --- | --- |
| Overall Product Wt. Gm Dryness, gm | 130.96/11.9 | 130.11/1.7 |
| 1 | 0.04 | 0.04 |
| 2 | 2.38 | 0.61 |
| 3 | 11.70 | 5.92 |
| Insult Time, Sec. |  |  |
| 1 | 11.70 | 10.9 |
| 2 | 48.4 | 11.1 |
| 3 | 32.7 | 12.1 |

As shown in the above table, the insult time for a diaper comprising an absorbent core having a through single slit of 1 inch×5 inches is considerably lower as compared to the diaper which includes an absorbent core without an aperture. It is also noted that the dryness is remarkably lower when using an absorbent pad according to the present invention.

Additional tests were conducted to determine the effect that slit size in the pad (length) on the insult time, in seconds. The test procedure was essentially the same as hereinbefore using similar diapers; one for control (without a slit) and others have 1 inch wide slit but slit lengths of 10 inches, 7 inches and 4 inches, respectively. The results are shown in Table 2 below.

TABLE 2

| Sample No. | Control | 10 inch slit | 7 inch slit | 4 inch slit |
| --- | --- | --- | --- | --- |
| 1 | 21 | 19 | 17 | 16 |
| 2 | 35 | 18 | 18 | 17 |
| 3 | 50 | 25 | 23 | 32 |

The diaper with 10 inch and 7 inch slit exhibited liquid run offs on the second and third runs. Liquid was observed coming up through the slit in the absorbent pad from outside of the dosing ring.

In making the absorbent article of the present invention, the top or cover sheet 228 conveniently made of spunbond nonwoven polypropylene which is available from First Quality Fibers, Inc., McElhattan, Pa. The acquisition layer 232 is usually made of chemically or thermally bonded nonwoven polyester polypropylene fibers available from, BBA Nonwovens, Simpsonville, N.C. Preferably the width of the acquisition layer 332 is 3 to 5 inches wide. The abosorbent pad 230 may be made of mixture wood pulp fibers (fluff) and superabsorbent polymers such as IM 7000 series available from Clariant Products, Inc., Portsmouth, Va., and Chemdal 200 Series, available from Chemdal, Inc., Palatin, Ill. Alternatively, the absorbent pad 230 may be of dual construction, in which case the absorbent polymer may be securely positioned between layers of the absorbent material.

The backing layer 234 may be a polyethylene backing film and is generally non-porous and is liquid, air and vapor impermeable. This layer is placed under the absorbent layer 230 in order to prevent the body exudates from leaking and thus soiling the user's bed and clothing. This film usually covers at least the area under the absorbent pad 230. In a preferred construction, the backing film 234 is adhesively or thermally laminated to the nonwoven backsheet 226, which itself is made of spunbond nonwoven polypropylene available from First Quality Fibers, McElhattan, Pa. Polyethylene suitable as backing film for making the diapers of this invention are available from Clopay Plastics, Cincinnati, Ohio. Alternatively, a layer of hydrophilic tissue may be used made of cellulosic fibers bonded together thermally, chemically or by the use of suitable sizing agents placed between the absorbent pad and the backing film. For improved effectiveness, the hydrophobic tissue may be laminated (cold or hot) to the nonwoven backsheet.

While the use of the absorbent pad of this invention has been described in connection with a breathable diaper, it must be understood that such description is for the purpose of illustration and is not intended to be a limitation on the use of this pad. Other types of diapers and briefs, and other absorbent articles such as sanitary napkins or pull ups may incorporate these pads in order to improve their liquid absorption.

Also, the backsheet used in the absorbent articles contemplated by the present invention may be a single film which is liquid-impermeable but vapor permeable or it may be a composite sheet made of a liquid-impermeable and vapor permeable film adherent to a layer of nonwoven material. The term "backsheet" as used herein is intended to encompass all such films and composites. Other changes and modifications may be made which are obvious from the foregoing detailed description.

What is claimed is:

1. A disposable absorbent article comprising:
   (a) a liquid-pervious topsheet,
   (b) a backsheet having a top surface and a rear surface,
   (c) a crotch region,
   (d) a single liquid absorbent pad disposed between said topsheet and said backsheet, said liquid-absorbent pad having a crotch region, a top surface and a bottom surface and a single elongated through slit extending from said top surface to said bottom surface of said liquid absorbent pad, said slit being from about 0.5 to about 1.5 inches wide and from about 2 to about 10 inches long and wherein said slit is disposed within the crotch region of said absorbent pad,
   wherein said topsheet is continuous over the area defined by said slit.

2. A disposable absorbent article as in claim 1 wherein said liquid absorbent pad is made of a material comprising a mixture of fluff and superabsorbent polymer (SAP).

3. A disposable absorbent article having a disposable absorbent pad as in claim 2 wherein the amount of SAP is from about 3 to about 80 weight percent of said fluff-SAP mixture.

4. A disposable absorbent article as in claim 2 wherein said liquid absorbent pad is defined by a pair of opposed longitudinal sides and a pair of opposed lateral sides, said slit being defined by a pair of opposed longitudinal sides and a pair of opposed lateral sides, a fluff-SAP mixture enriched zone defined between longitudinal sides of said absorbent pad and longitudinal sides of said slit, and lateral sides of said absorbent pad and lateral sides of said slit, and wherein the basis weight of the fluff-SAP mixture in said zone is greater than the basis weight of fluff-SAP mixture in the remaining portion of said absorbent pad.

5. A disposable absorbent article having a disposable absorbent pad as in claim 4 wherein the amount of SAP in said fluff-SAP mixture is from about 3 to about 80 weight percent of said mixture.

6. A disposable absorbent article as in claim 1 wherein said crotch region has a front edge and a back edge, said absorbent pad has a front edge and a back edge, said elongated slit has a front edge and a back edge and wherein the distance between the front edge of said slit and the front edge of said crotch region is less than the distance between the back edge of said slit and the back edge of said crotch region.

7. A disposable absorbent article comprising:
   (a) a liquid-pervious topsheet having opposed lateral ends,
   (b) a liquid-impervious backsheet having opposed lateral ends,
   (c) a crotch region,
   (d) a liquid absorbent pad disposed between said topsheet and said backsheet, said liquid-absorbent pad having a crotch region, a longitudinal axis, a transverse axis, a top surface and a bottom surface, opposed longitudinal sides and opposed lateral sides, and a single elongated through slit extending from said top surface to said bottom surface, said slit having a width of from about 0.5 to about 1.5 inches and a length of from about 2 to about 10 inches, and wherein said slit is disposed within said crotch region of said absorbent pad;
   wherein said topsheet is continuous over the area defined by said slit.

8. A disposable absorbent article as in claim 7 wherein said liquid-absorbent pad is made of a material comprising a mixture of fluff and superabsorbent polymer (SAP).

9. A disposable absorbent article having a disposable absorbent pad as in claim 8 wherein the amount of SAP is from about 3 to about 80 weight percent of said fluff-SAP mixture.

10. A disposable absorbent article as in claim 8 wherein said liquid absorbent pad is defined by a pair of opposed longitudinal sides and a pair of opposed lateral sides, said slit being defined by a pair of opposed longitudinal sides and a pair of opposed lateral sides, a fluff-SAP mixture enriched zone defined between longitudinal sides of said absorbent pad and longitudinal sides of said slit, and lateral sides of said absorbent pad and lateral sides of said slit, and wherein the basis weight of the fluff-SAP mixture in said zone is greater than the basis weight of fluff-SAP mixture in the remaining portion of said absorbent pad.

11. A disposable absorbent article having a disposable absorbent pad as in claim 10 wherein the amount of SAP in said fluff-SAP mixture is from about 3 to about 80 weight percent of said mixture.

12. A disposable absorbent article as in claim 7 wherein said crotch region has a front edge and a back edge, said absorbent pad has a front edge and a back edge, said elongated slit has a front edge and a back edge and wherein the distance between the front edge of said slit and the front edge of said crotch region is less than the distance between the back edge of said slit and the back edge of said crotch region.

13. A breathable disposable absorbent article comprising:
   (a) a backsheet having opposed side edges and opposed front waist and back waist edges connecting said side edges, each of said side edges having a medial cutout portion, (b) a top sheet having opposed side edges and corresponding opposed front waist and back waist edges connecting said side edges, each of said side edges having a medial cutout portion, said backsheet and said topsheet being sealed together at their respective edges so as to form a unitary structure having leg openings defined by said medial cutout portions, (c) a single liquid absorbent pad having a crotch region disposed between said topsheet and said backsheet, said liquid-absorbent pad having a top surface and a bottom surface and a single elongated through slit extending from said top surface to said bottom surface of said liquid absorbent pad, said slit being from about 0.5 to about 1.5 inches wide and from about 2 to about 10 inches long and wherein said slit is disposed within said crotch region of said absorbent pad, (d) at least one releasable fastening means at each of said side edges disposed at one end of said absorbent article, and (e) at least one zone made of a perforated polymeric film disposed on said backsheet, said zone having an inside surface adherent to said backsheet, and an opposed outer surface adapted to be releasably engaged to said fastening means, wherein said topsheet is continuous over the area defined by said slit.

14. A breathable disposable absorbent article as in claim 13 having a pair of spaced apart landing zones, each landing zone having an inside surface adherent to said backsheet, and an opposed outer surface adapted to be releasably engaged to said fastening means.

15. A breathable disposable absorbent article as in claim 13 wherein said liquid absorbent pad is made of a material comprising a mixture of fluff and superabsorbent polymer (SAP).

16. A breathable disposable absorbent article as in claim 15 wherein the amount of SAP is from about 3 to about 80 weight percent of said fluff-SAP mixture.

17. A breathable disposable absorbent article as in claim 15 wherein said liquid absorbent pad is defined by a pair of opposed longitudinal sides and a pair of opposed lateral sides, a slit being defined by a pair of opposed longitudinal sides and a pair of opposed lateral sides, a fluff-SAP mixture enriched zone defined between longitudinal sides of said absorbent pad and longitudinal sides of said slit, and lateral sides of said absorbent pad and lateral sides of said slit, and wherein the amount of the fluff-SAP mixture in said zone is greater than the amount of fluff-SAP mixture in the remaining portion of said absorbent pad.

* * * * *